United States Patent [19]
Kittle

[11] Patent Number: 5,853,050
[45] Date of Patent: Dec. 29, 1998

[54] COMPOSITION AND METHOD FOR GENERATING A FOAM BARRIER AND METHODS OF USE THEREOF

[75] Inventor: Paul A. Kittle, Concordville, Pa.

[73] Assignee: Rusmar Incorporated, West Chester, Pa.

[21] Appl. No.: 852,333

[22] Filed: May 7, 1997

[51] Int. Cl.⁶ .............................. A62C 3/00; A62D 1/04; B01J 13/00; B05D 5/00
[52] U.S. Cl. .............................. 169/47; 252/3; 252/8.05; 252/307; 422/40; 427/244
[58] Field of Search .............................. 252/3, 8.05, 307; 422/40; 427/244; 169/49, 47

[56] References Cited

U.S. PATENT DOCUMENTS

| | | | |
|---|---|---|---|
| 4,127,383 | 11/1978 | Johnston et al. | 252/307 X |
| 4,171,407 | 10/1979 | Elser et al. | 428/500 |
| 4,390,450 | 6/1983 | Gibson et al. | 252/307 |
| 4,424,133 | 1/1984 | Mulligan | 252/8.05 |
| 4,874,641 | 10/1989 | Kittle | 427/244 |
| 4,923,903 | 5/1990 | Alm et al. | 521/65 |
| 5,124,363 | 6/1992 | Stern | 252/3 X |
| 5,133,991 | 7/1992 | Norman et al. | 427/244 X |
| 5,215,786 | 6/1993 | Kittle | 427/244 |
| 5,225,095 | 7/1993 | DiMaio et al. | 252/307 |
| 5,382,285 | 1/1995 | Morrison | 106/122 |
| 5,434,192 | 7/1995 | Thach et al. | 521/50 |

FOREIGN PATENT DOCUMENTS 900868  7/1962  United Kingdom .

OTHER PUBLICATIONS

K. Clare, "Applications of Novel Biogums", CHEMSPEC, 1988 Symposium.

N. Portney et al, U.S. Statutory Invention Registration No. H507, published Aug. 2, 1988.

The Merck Index, 10th Edition (1983) Publ. By Merck & Co., Inc., p. 1258.

*Primary Examiner*—Richard D. Lovering
*Attorney, Agent, or Firm*—Howson and Howson

[57] ABSTRACT

Compositions useful in generating a foam particularly well adapted for use as a barrier are provided. These compositions contain keratin protein, a modified starch composed of at least 75% amylopectin, a ferrous ion component, and a dispersant.

42 Claims, 5 Drawing Sheets

COMPOSITION AND METHOD FOR GENERATING A FOAM BARRIER AND METHODS OF USE THEREOF

FIELD OF THE INVENTION

The present invention relates generally to foam compositions, and more particularly, to foam compositions useful as barriers, particularly for landfill coverage and in extinguishing coal mine fires.

Background of the Invention

The use of foam compositions and their advantages over soil in covering landfills has been described previously. See, e.g., U.S. Pat. No. 4,874,641 and U.S. Pat. No. 5,215,786. These foams serve to protect the atmosphere from deleterious materials and odors which would escape from the landfill. Further, these foams are advantageous over dirt in that they eliminate the need to place and compact dirt, which requires significant labor, heavy equipment, and consumes valuable space.

However, the foam barriers described in the prior art have been found to be characterized by insufficient persistence for multiple day usage, i.e., the barrier provided does not maintain the desired physical integrity for periods in excess of about twenty-four hours. Further, the barrier foams are susceptible to both dilution and physical damage from rain.

U.S. Pat. No. 5,133,991 and U.S. Pat. No. 5,225,095 describe protein-based materials useful as foams. However, these compositions have been found to be subject to physical instability and chemical degradation, resulting in decreased foamability and poor foaming performance.

Biodegradable foams, characterized by their ability to maintain their physical integrity over a period of three to four days, as well as maintain their physical integrity when exposed to rain, are needed in the art. Further, compositions, useful in generating these durable foams, which exhibit good chemical and physical stability, allowing ease of manufacturing are needed.

SUMMARY OF THE INVENTION

The present invention provides foamable compositions which are capable of bulk storage without significant degradation over long intervals of time.

In one aspect, the present invention provides a mixture which may be diluted to form a concentrate of the invention or a foamable solution. This mixture contains (on a 100% dry basis) about 15% to about 20%, by weight, hydrolyzed keratin protein, about 6% to about 8% ferrous ion, and preferably about 30% to about 40%, by weight, when in the form of ferrous sulfate heptahydrate; about 10% to about 15%, by weight, of a dispersant; and about 25% to about 50%, by weight, modified starch consisting of at least about 75% amylopectin, and preferably, at least about 99% amylopectin.

In another aspect, the present invention provides an aqueous concentrate which upon dilution forms a foamable solution. The concentrate contains about 2% to about 8%, by weight, hydrolyzed keratin protein; about 1% to about 4% ferrous ion, and preferably, about 5% to about 20%, by weight, when in the form of ferrous sulfate heptahydrate; about 1% to about 10%, by weight, of a dispersant; about 1% to about 7.5%, by weight, modified starch; a pH modifier in an amount sufficient to adjust the pH to between about 6.0 and 6.5; and water.

In yet another aspect, the present invention provides a foamable solution according to the invention. The solution is preferably produced by dilution of an aqueous concentrate of the invention with water at a ratio of between 3 to 10 parts by weight water to 1 part by weight concentrate.

In still another aspect, the present invention provides a method of generating a biodegradable foam. This method involves the steps of providing a foamable solution of the invention and agitating the diluted concentrate in the presence of air, thereby generating the foam.

In a further aspect, the present invention provides a foam generated by the method of the invention.

In yet a further aspect, the present invention provides a method of forming a barrier layer between a substrate and the atmosphere. This method involves providing a foamable solution of the invention, generating a biodegradable foam from the diluted concentrate, and applying the foam to a substrate.

Finally, the invention provides a unique composition and method for extinguishing mine fires.

Other aspects and advantages of the present invention are described further in the following detailed description of the preferred embodiments thereof.

DETAILED DESCRIPTION OF THE INVENTION

The present invention provides novel compositions useful in forming foams, methods for generating foams, and foams produced by these methods. Advantageously, the compositions of the invention are characterized by superior stability and, particularly, are not subject to the chemical oxidation and physical degradation characteristic of prior art foamable compositions. Further, the foams generated from the compositions of the invention are characterized by improved ability to withstand deterioration caused by exposure to rain and aging.

The present invention provides a dry mixture, an aqueous concentrate, a foamable solution, and a foam, which will be discussed in more detail below. Each of these compositions of the invention contains hydrolyzed keratin protein, modified starch which is primarily amylopectin in content, a ferrous ion component, and a dispersant. These ingredients, as well as a number of optional ingredients which may be included in the compositions of the invention, are discussed below.

The protein component of the compositions of the invention is hydrolyzed keratin protein. The hydrolyzed keratin protein may be dry, such as that which is available from, e.g., Industria Suma Ltda. [Brazil], or in solution from other sources, e.g., Croda Kerr [England], Angus Fire [Canada], National Foam [US]. Preferably, the keratin protein utilized in the present invention is derived from animal hooves and horns. Although less preferred, other suitable sources of protein may be readily determined and utilized.

The compositions of the invention further contain starch, and more particularly, starch which has been modified to remove its anionic characteristics. Briefly, and without wishing to be bound by theory, the inventor has found that the use of starch in its natural anionic state is undesirable because it contributes to the instability of the foaming composition by reacting with the other components, particularly the cationic ferrous ion component, discussed below, resulting in unsatisfactory foam generation and performance.

In one embodiment, the modified starch of the invention is characterized by having been hydroxyalkylated using known processes. This process has the effect of removing the anionic characteristics of the starch. Suitable hydroxyalkylated starches may be readily purchased from commercial sources, e.g., National Starch (Instant Pure-Flo F) or Cerestar (Instant Gelex). In one currently preferred embodiment, the starch is hydroxypropylated.

Further, the starch of the invention is desirably characterized by having an amylopectin content which exceeds the amylose content, i.e., an amylopectin content of at least about 75%. More desirably, the starch contains between about 90% to about 100% amylopectin, and most desirably, at least about 99% amylopectin. Starch containing suitable amylopectin contents may be derived from waxy maize or waxy sorghum, obtained from commercial sources, e.g., National Starch & Chemical or Cerestar. Further, mixtures of one or more starches from these or other sources which provide starch of the appropriate amylopectin content may be utilized in the invention. For convenience, the starch is desirably pregelatinized, obviating high temperature, high pressure, cooking in order to obtain gelatinization or solubility.

The mixture of the invention further contains a ferrous ion component, which is preferably in the form of ferrous sulfate ($FeSO_4$). The ferrous sulfate may be obtained from commercial sources, and is preferably in the form of ferrous sulfate heptahydrate ($FeSO_4.7H_2O$). However, other sources of ferrous ion or ferrous sulfate may be substituted, as desired.

Optionally, many commercially available dispersants may be added to enhance the dispersion of the ingredients. Such dispersants are well known to those of skill in the art and are not a limitation of the present invention. Examples of suitable dispersants include sodium lignosulfonate and ammonium lignosulfonate, which are available commercially, e.g., sodium lignosulfonate [available commercially as Maraperse N-22 from Lignotech USA, Inc.]. Alternatively, suitable dry dispersants may be readily selected.

As desired, a composition of the invention is provided with an odorant which masks the odor associated with the protein utilized in the mixture. Currently, the preferred odorant is cinnamon, which is desirably provided in the form of cinnamon oil dispersed on a solid substrate, e.g., polymeric beads. This odorant is commercially available, e.g., from Horizon Chemical, Newark, Del. (catalog #2620). However, other suitable odorants, which do not affect foam performance may be readily determined and substituted by one of skill in the art.

Preferably, the composition of the invention further contains an amount of a pH modifier sufficient to provide a concentrate, foamable solution and foam having a pH between about 6.25 to about 7, and more preferably about 6.5. As with the other ingredients described herein, an appropriate pH modifier may be readily selected by one of skill in the art, and may be added in dry form to the mixture described above, or in liquid form, to the aqueous concentrate or foamable solution described herein. Currently, a preferred pH modifier is ammonium hydroxide.

Optionally, a biocide may be added to prevent the decomposition of the mixture or concentrate by bacteria. Any number of biocides may be used such as Kathon (Rohm and Haas, Co.), Nipacide BK, Nipacide BCP or Nipacid MX (Nipa Laboratories). Suitable amounts of the biocide may be readily determined and adjusted by one of skill in the art.

Where desired, the flow characteristics of the foam can be modified by the addition of small amounts of foam boosters, allowing certain foam applications to be smoother and more effective without sacrificing, weather and aging performance. Suitable foam boosters are well known and may be readily selected by those of skill in the art. Currently, a preferred modifier is a glycol ether, many of which are known to those of skill in the art. One particularly desirable glycol ether is diethyleneglycol monobutylether.

In one aspect, the present invention provides a dry mixture, which upon dilution, can be used to produce a concentrate of the invention. Alternatively, the dry mixture of the invention may be diluted and used directly for generation of a foam of the invention. Such a dry mixture is advantageous for a variety of reasons. For example, the dry mixture permits reducing storage volumes and shipping costs as compared to more dilute compositions.

The dry mixture of the invention contains the components described above. Suitably, the hydrolyzed keratin protein is present in an amount between about 15% to about 20%, by weight, and more desirably, about 19%, by weight, of the mixture. The modified starch is present in an amount between about 25% to about 50%, by weight, and more preferably, about 30%, by weight. The ferrous ion component is present in an amount between about 6% to about 8%, by weight. However, one of skill in the art can readily adjust these percentages as needed, depending upon the source of ferrous ion. Preferably, the source is ferrous sulfate heptahydrate which is present in an amount between about 30% to about 40%, by weight, and, more preferably, about 37%, by weight. Generally, the dispersant is present in the dry mixture in an amount between about 10% to about 15%, by weight. However, the amount of dispersant may be readily adjusted depending upon the compound or compounds selected. For example, where the dispersant is ammonium lignosulfonate or sodium lignosulfonate, the dispersant is preferably present in an amount of about 12%, by weight.

Appropriate amounts of the optional ingredients described above for inclusion in the dry mixture of the invention may be readily determined by one of skill in the art. Alternatively, one or more of these optional ingredients, e.g., a glycol ether, may be added as desired upon dilution of the dry mixture.

In another aspect, the present invention provides an aqueous concentrate which upon dilution with water results in a foamable solution useful for generating a foam of the invention. The inventor has found that the modified starch component, when utilized in the aqueous concentrate of the invention, acts as a protective colloid which assists in protecting the ferrous ion component from oxidation during shipping and storage, even when exposed to atmospheric air. Thus, in contrast to known foamable concentrates, the concentrate of the invention is stable and well adapted for shipment and storage in aqueous form.

Desirably the concentrate of the invention contains, at a minimum, about 2% to about 8%, by weight, hydrolyzed keratin protein, about 1% to about 7.5%, by weight, modified starch as described herein; about 1% to about 4%, by weight of ferrous ion, and about 1% to about 10%, by weight, dispersant, and water. One of skill in the art can readily adjust these percentages depending upon the source of this component. Preferably, the ferrous ion component is ferrous sulfate heptahydrate which is present in an amount of between about 5% to about 20%, by weight. The concentrate further contains sufficient amounts of a pH modifier to adjust the pH of the concentrate to between about 6.5 to about 7.0, and other desired optional components, as discussed above.

For example, when present in the concentrate, the odorant is present in an amount up to about 1%, by weight, and the biocide is present in an amount between about 0.1% to about 1%, by weight, of the concentrate. Generally, when present in the concentrate, any foam boosters utilized are present in an amount up to about 2%, by weight, and most desirably, about 0.75% to about 2%, by weight. However, these amounts may be readily adjusted as needed by those skilled in the art.

In order to prepare the foamable solution of the invention, the dry mixture or, alternatively, the aqueous concentrate, is diluted with an appropriate amount of water. Where desired, the formulation of the dry mixture or concentrate may be adjusted in accordance with the dilution to be utilized by the customer in generating the foam of the invention. Generally, a concentrate of the invention is diluted at a ratio of between 3 to 10 parts by weight water to 1 part by weight concentrate to obtain a foamable solution having an actives concentration of between about 1 to about 5%, by weight, and preferably about 2 to about 4 wt %. However, one of skill in the art can readily prepare other desired concentrates and dilutions, having been provided with the ranges and guidelines described.

In one currently preferred embodiment, a concentrate of the invention is diluted with about 6.5 parts water to 1 part concentrate, resulting in a foamable solution of the invention. Such a dilution factor is particularly desired, for example, when about 0.5" or less rain is anticipated, or it is anticipated that the foam will remain uncovered only overnight. In such an embodiment, the concentrate most preferably contains about 3.2%, by weight, hydrolyzed keratin protein, about 6%, by weight, ferrous sulfate heptahydrate, and modified starch in an amount of about 5%, by weight, with the balance being water. The resulting foamable solution contains about 2 wt % actives, with the balance being water.

In another preferred embodiment, the same concentrate of the invention as above is diluted with about 3.75 parts water to 1 part concentrate. Such a dilution factor is particularly desirable, for example, when more than about 0.5" of rain is anticipated and/or the foam is expected to remain uncovered for longer than 24 hours. The resulting foamable solution contains about 4 wt % actives, with the balance being water.

The present invention further provides a method of generating a foam utilizing a composition of the invention. The foam is generated using known methods, e.g., by agitating a foamable solution of the invention in the presence of air. One apparatus for this purpose forces the foamable solution through a restricted passage at a high pressure and injects air into the solution downstream of the restriction. The foam may then be sprayed onto the substrate through a nozzle.

At the time of foam production, the foamable solution may be pumped at, for example, 400 to 500 psig, through a flow controlling orifice at a pre-determined flow rate. Downstream of the liquid flow control orifice, air is injected and mixed with the liquid stream. This may be achieved by using an air orifice to control the flow in the same manner as the liquid side of the system. An air compressor generates a regulated air pressure. After the two streams are combined, the mixture passes through an exit, such as a hose which may or may not have a distribution nozzle attached. The foam can then be distributed over the area to be covered, by manually directing the hose nozzle. Similarly, the output may be directed into a multiported manifold for distribution. This manifold depending upon its size and the flow rate of foam, may be used to distribute the foam either manually or mechanically via attachment to a suitable vehicle. The vehicle may be towed or self-propelled, and may be completely self-contained in that it may have the liquid storage tank, air compressor, pumping systems, distribution system, and drive mechanism all in one integrated unit.

The foam may be applied under widely varying atmospheric temperature conditions including freezing. At atmospheric temperatures below freezing the foam surface simply freezes.

Thus, the present invention further provides a foam generated by the methods of the invention. The resulting foam is particularly useful as a barrier layer between a substrate and the atmosphere. However, other uses of the foam of the invention will be readily apparent to one of skill in the art. Desirably, a foam of the invention exhibits the following characteristics: the foam's drain time is very long (slow) and can be extended by increasing the concentration (i.e., decreasing the dilution ratio); the foam's stiffness exhibits the capability of covering the vertical surface of stacked bales of trash, as well as more conventional sanitary landfill working face surfaces; the foam's persistence is excellent, showing no noticeable changes in ordinary overnight exposure, even up to about 100 hours, when the concentration is increased by decreasing the dilution ratio; and the foam's weather resistance is equal or superior to soil, exhibiting the capacity to withstand 0.5" of overnight rainfall, and up to about 1.0" to 1.5" of rainfall over extended exposures and at higher concentrations.

The examples below illustrate the preparation of mixtures, concentrates and foams of the invention. Advantageously, and in contrast to prior art compositions, the order of addition of the ingredients is not particularly critical. However, proceeding with the hydration and dissolution of the modified starch as the first step may facilitate the efficiency of the process. The following examples are illustrative only and do not limit the scope of the invention.

EXAMPLE 1

An exemplary dry mixture according to the present invention is prepared by mixing the following ingredients:

| Ingredient | Weight Percent (%) |
| --- | --- |
| Hydrolyzed Keratin Protein | 19.64 |
| Modified Starch | 30.66 |
| Cinnamon Powder | 0.63 |
| Ferrous Sulfate Heptahydrate | 36.79 |
| Dispersant | 12.28. |

To produce the foamable solution, the above mixture is dissolved in water with glycol ether, if desired, followed by a pH adjustment.

EXAMPLE 2

An exemplary concentrate of the invention is prepared by mixing the following ingredients:

| Ingredient | Weight Percent (%) |
| --- | --- |
| Keratin Protein Hydrolysate | 3.20 |
| $FeSO_4 \cdot 7H_2O$ | 6.00 |
| Dispersant | 4.00 |
| Modified Starch | 5.00 |
| Diethyleneglycol monobutylether | 0.75 |
| Ammonium hydroxide | 0.30 |
| Biocide | 0.09 |
| Cinnamon | 0.10 |
| Water | 80.56. |

Briefly, diethyleneglycol monobutylether was added to ambient temperature water. To this mixture, a pre-gelatinized, hydroxypropylated, >99% amylopectin starch (purchased commercially as Instant Gelex) was added with good mixing as the hydrated and dissolved starch generates very high viscosity, although the mixture is very shear thinning. After the starch was completely hydrated and mixed, the ferrous sulfate heptahydrate was added. The dispersant [ammonium lignosulfonate, Norlig TSFL-4, Lignotech USA, Inc.] was added next, followed by the dry keratin protein hydrolysate. The entire mixture was stirred until homogenous, and then the ammonium hydroxide added, bringing the pH into the 6.5–7.0 range. Some inhomogeneity occurs upon the addition of the ammonium hydroxide, but thorough stirring re-homogenizes the mixture. The final steps add the cinnamon powder and the biocide. Stirring was continued until homogeneous consistency was obtained. The material was transferred to the storage vessel of choice.

The resulting concentrate is characterized by having a solids content of 14.20%±0.10%; pH 6.5–7.0 @ room temperature; viscosity, immediately, Brookfield spindle #4, room temperature, 22000, 14000, 75000, and 5000 cps at 6, 12, 30, 60 rpm, respectively. After sitting at rest overnight, the viscosity increases in the same order, to 33000, 18000, 10000, 7000 cps.

To prepare the foamable solution, the resulting concentrate is diluted at a ratio of 6.5 parts water to 1 part concentrate. The resulting solution was foamed through a 20 gallons per minute foam system at 100 psig air pressure to produce a foam. Other suitable foaming conditions may be readily determined and utilized.

EXAMPLE 3

Another exemplary concentrate of the invention is prepared by mixing the following ingredients:

| Ingredient | Weight Percent (%) |
| --- | --- |
| Hydrolyzed Keratin Protein | 4.20 |
| $FeSO_4 \cdot 7H_2O$ | 8.00 |
| Dispersant | 5.30 |
| Modified Starch | 6.65 |
| Diethyleneglycol monobutylether | 1.00 |
| Ammonium hydroxide | 0.40 |
| Biocide | 0.09 |
| Cinnamon | 0.10 |
| Water | 74.26. |

The concentrate is prepared as described in Example 2. The concentrate is characterized by having a solids content of 18.50%±0.10%; pH, 6.5–7.0 @ room temperature; viscosity, immediately, Brookfield, spindle #4, room temperature, 32000, 22000, 13000, and 8900 cps at 6, 12, 30, 60 rpm, respectively.

The foaming solution is prepared as described in Example 2 above, with the exception that the concentrate is diluted at a ratio of 9 parts water to 1 part concentrate, yielding the same diluted, to be foamed liquid as in Example 2.

EXAMPLE 4

The following aging and drain time data was obtained using foam compositions of the invention generated from a concentrate as described in the examples above.

A. Drain Time Performance

Figure 1:
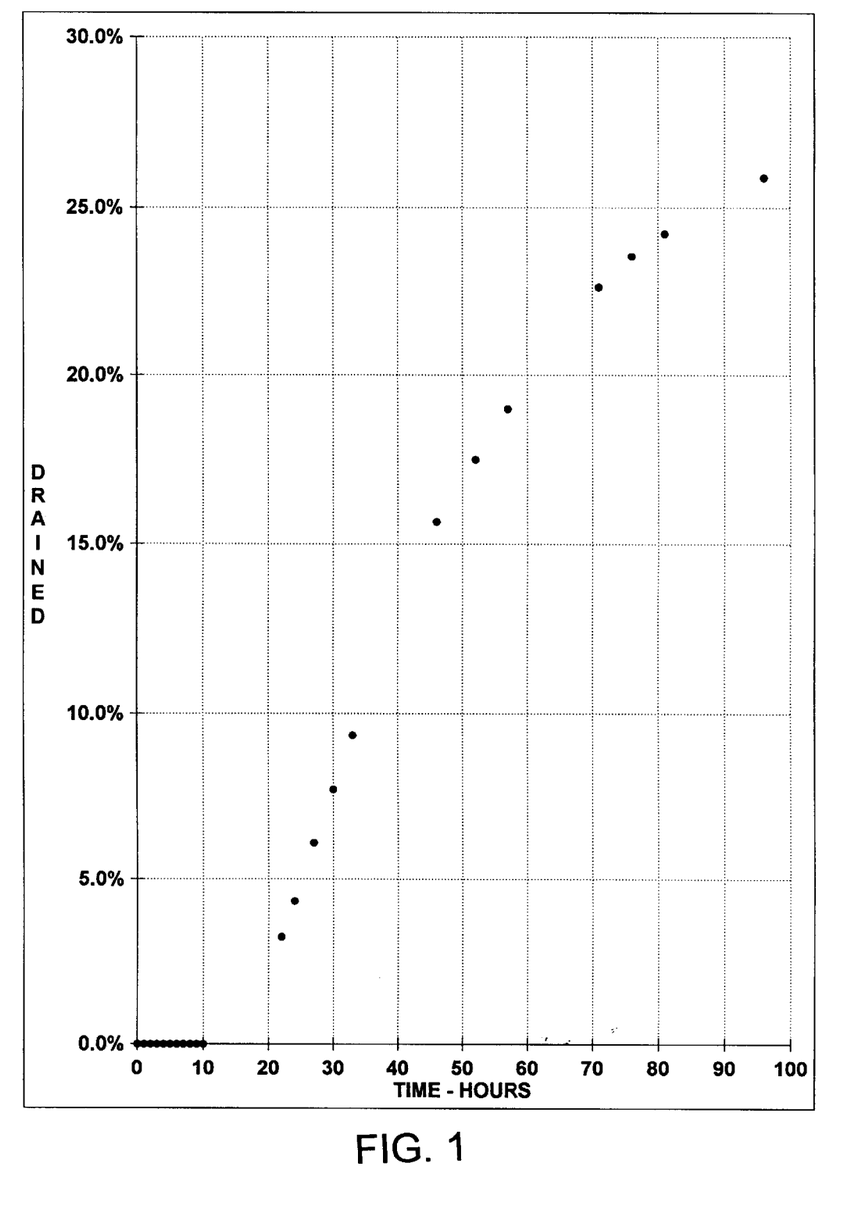
FIG. 1 is a drain time performance curve of a foaming composition of the invention generated from a concentrate having a dilution ratio of 7.5. Drain time was determined at a temperature range of between 15°–20° C. and ambient relative humidity.

Drain time of a foam generated essentially as described in Example 2 was measured over a period of 100 hours under different temperature and humidity conditions. Drain time was determined as described in U.S. Pat. No. 4,874,641. In a first experiment, drain time was determined at a temperature between 15°–20° C. and at ambient relative humidity. These results are provided in FIG. 1. These results show that within the first ten hours the amount of drained material was zero, while at the end of the first "day" (approximately 25 hours), only 5% of the foam mass had drained.

Figure 2:
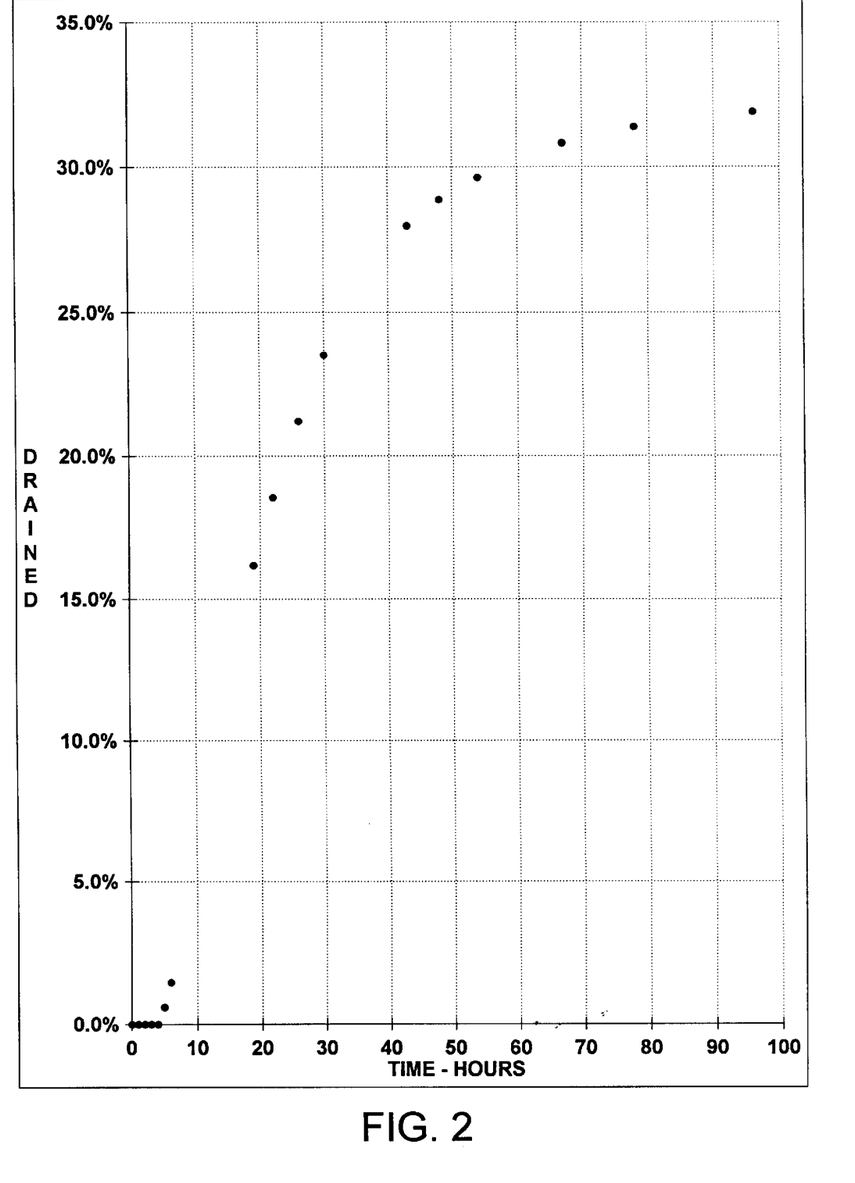
FIG. 2 is a drain time performance curve of a foaming composition of the invention generated from a concentrate having a dilution ratio of 7.5. Drain time was determined at a temperature of 40° C. and a relative humidity of 25%.

In a second experiment, drain time was determined at a temperature of 40° C., and a relative humidity of 25%. These results are provided in FIG. 2. These results show that at this elevated temperature, 40° C. (104° F.), the initial drainage occurs at the sixth hour, and, by comparison, 5% drainage has resulted in nine hours.

Figure 3:
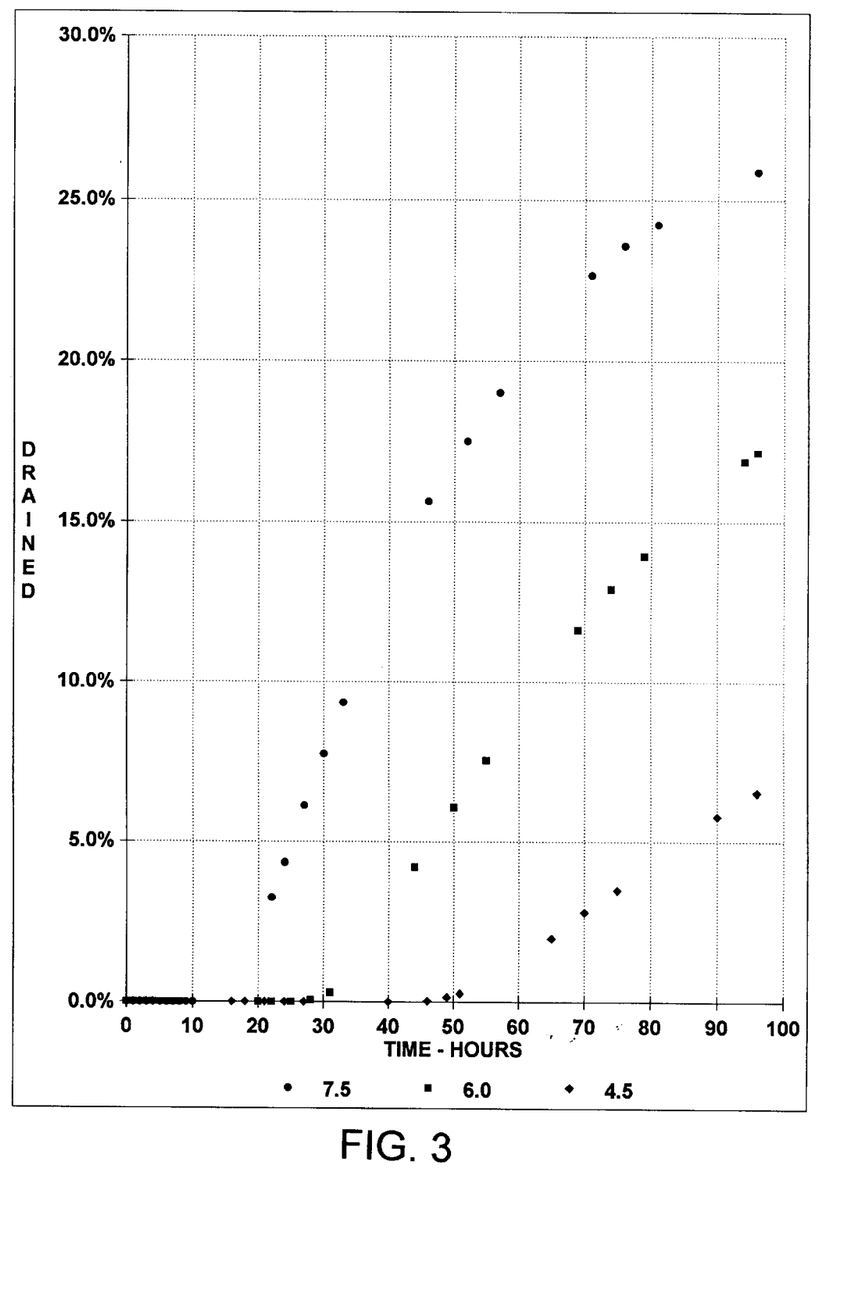
FIG. 3 is a drain time performance curve of foaming compositions of the invention generated from concentrates having a dilution ratio of 7.5 (circles), 6.0 (squares), and 4.5 (diamonds), respectively. Drain time was determined at a temperature of between 15°–20° C. and ambient relative humidity.
Figure 4:
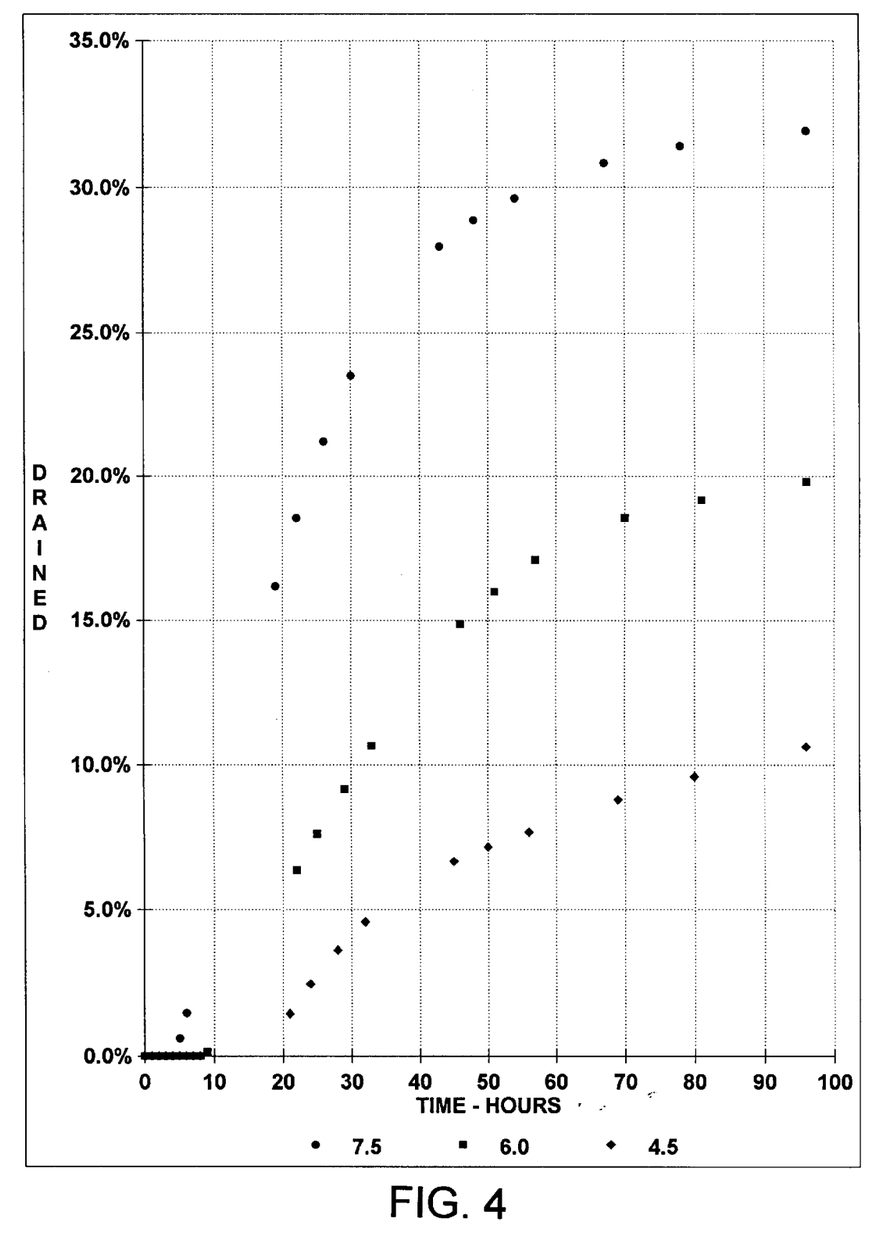
FIG. 4 is a drain time performance curve of foaming compositions of the invention generated from concentrates having a dilution ratio of 7.5 (circles), 6.0 (squares), and 4.5 (diamonds), respectively. Drain time was determined at a temperature of 40° C. and a relative humidity of 25%.

Using similar conditions to those described above, drain time of foams generated using varying dilution ratios, and particularly 7.5, 6.0, and 4.5, were determined. The 6.0 dilution was prepared as described in Example 2, with the exception that the concentrate was diluted with 5.0 parts water to 1 part concentrate yielding a 16.7% solids content. The 4.5 dilution was similarly prepared, with the exception that the concentrate was diluted with 3.5 parts water to 1 part concentrate, yielding a 22.2% solids content. These results are illustrated in FIGS. 3 and 4, respectively. As shown therein, the effect of decreasing the dilution ratio (i.e., increasing the concentration), delays the initiation of the drainage from 10 hours for the 7.5 dilution, to 27 hours for the 6.0 dilution, to 49 hours for the 4.5 dilution. Correspondingly, the 5% drainage times occur at 26 hours, 47 hours, and 85 hours.

B. Aging

Figure 5:
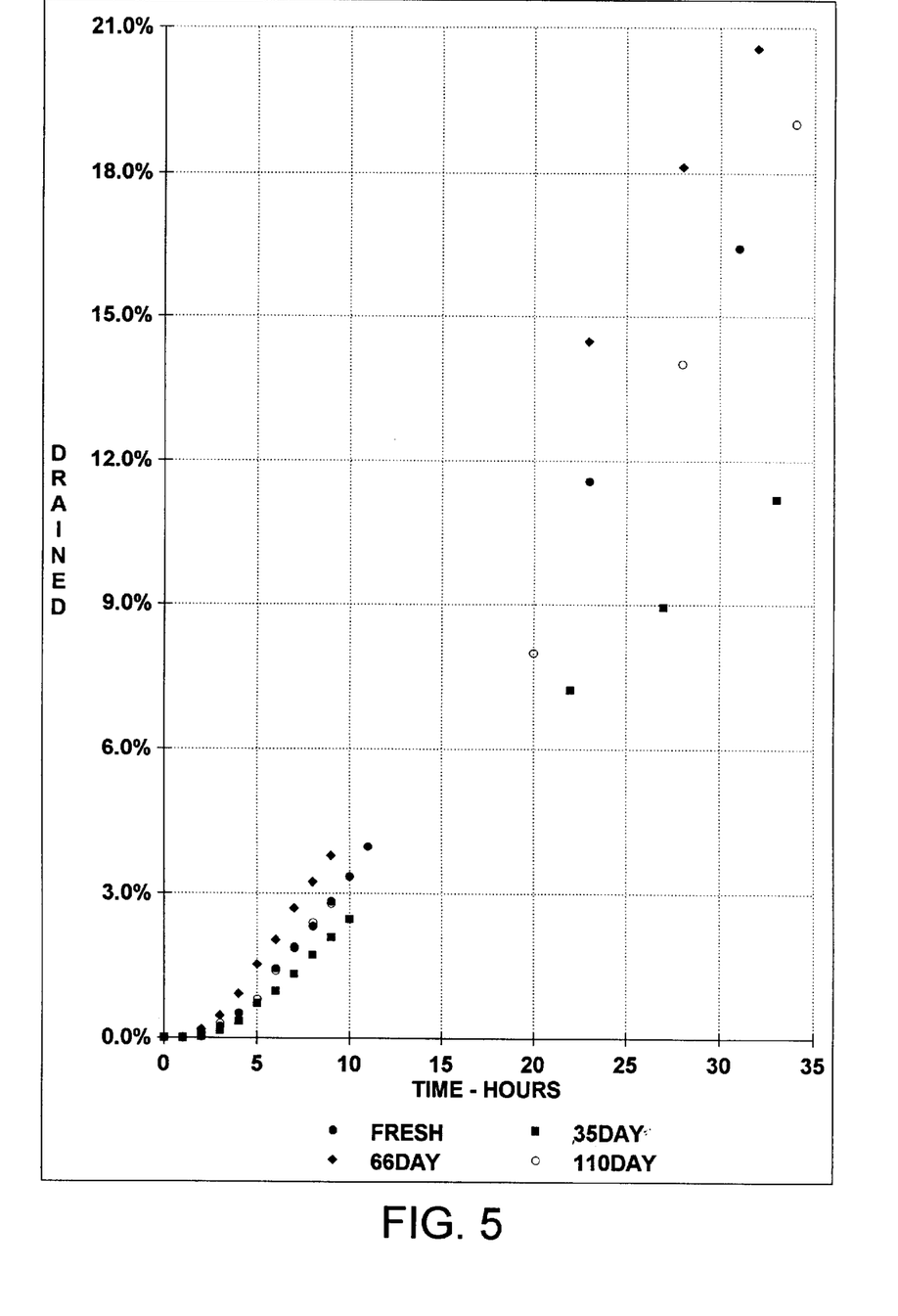
FIG. 5 is an aging curve illustrating the drain percentages as a factor of time, determined shortly following foam generation (fresh, solid circle), at 35 days (square), at 66 days (diamond), and at 110 days (open circle).

As illustrated in FIG. 5, drain time was determined shortly following foam generation (fresh), and at 35, 66, and 110 days. Briefly, the composition used for this aging study was production material transferred to a laboratory sized bulk storage system. As soon as the material was placed in the system, a sample was removed ("fresh"), and the drain time determined. In sequence, 35, 66 and 110 days later, the drain time data was redetermined on a "new" sample removed from the storage system. Each determination was performed identically, using the same drain time vessel.

These results demonstrate that the drain time of the foam is unaffected by the age of the stored material, even when the storage vessel is exposed to air. The variations between the various experiments are simply experimental scatter.

EXAMPLE 5

The weather performance data was obtained using a foam composition of the invention generated from a concentrate as described in the examples above.

A. The effect of wind

Wind is known to affect daily cover foam during the application by potentially blowing the foam away before it has reached the ground. The longer term effects can be potentially ascribed to erosion and/or dehydration. The following study has addressed all of these characteristics within the weather/wind parameters available during a demonstration program period.

(1) During application

The effect of wind during handline application is very significant, since the application is, by definition, unidirectional. Since applying foam "upwind", when the wind is strong is difficult, the potential thoroughness of the coverage can be restricted or reduced, if care is not taken.

Two handline applications, one on a test area and one on the working face, were executed in winds with gusts at 30+ mph. In both cases the coverage was evaluated as "excellent" and persisted overnight without degradation.

(2) Overnight and extended exposure

A self-propelled working face application was executed in 25–30 mph wind gusts, with the wind persisting throughout most of the evaluation period of 17 hours. The evaluation of the application was "excellent" without degradation overnight.

In another experiment, a self-propelled unit applied the foam to an entire working face during wind gusts at 25± mph on a Friday afternoon. The wind continued at the same level during the night, but dropped to the 10–15 mph range in the early morning of the next day, Saturday. On Sunday, the wind again increased to more than 30 mph during the afternoon, and remained at that level through Sunday night and early Monday morning. The temperature was above freezing for the entire exposure period, so the foam did not freeze.

The evaluation of the application was "excellent" and that rating continued through the Saturday morning inspection, 17 hours, and the Monday morning inspection, 63 hours.

C. The effect of precipitation—rain

Of the sixty-eight applications executed during this study, thirty-one were exposed to precipitation in the form of rain. The performance characteristics for the interaction of foam of the invention with rain was determined.

More particularly, foams of the invention containing dilutions of between 13.5% to 27.0% (weight percent D/R= 7.5 concentrate in the diluted liquid) were evaluated. The foams of the invention were applied to the surface at an average initial coverage of 98.5% and subsequently tested under a variety of conditions. Specifically, the amount of rain varied from less than 0.1" to a maximum of 0.47", and the exposure varied from overnight, 20 hours, to 100 hours, the following performance was observed.

The average final coverage was 94.3% and the average coverage degradation was 4.2%. This study and those which follow demonstrate that within the time periods, overnight to over extended weekends, at various concentrations, and varying rain condition, the foam performed satisfactorily.

D. The effect of temperature

Applied foam of the invention was exposed to temperatures down to 5° F. (−15° C.) and as high as the highest temperature reached during the program 70° F. (21° C.).

When tested below freezing conditions, the foam of the invention freezes when the temperature is lower than 32° F. (0° C.). When frozen, the foam matrix is rigid and immobilized. Drainage cannot occur because the water cannot move. This condition will be maintained as long as the frozen condition remains. If the freezing conditions are removed, allowing the foam to thaw, the foam returns to "normal" and the drainage process begins. No unusual performance characteristics are associated with the freezing event.

EXAMPLE 6

In the case of a mine fire, the aqueous concentrate utilized is as defined herein. However, quantities of ferrous ion at the higher end of the range provided herein are desirable, as the ferrous ion deposited as a coating on the mine surfaces serves as a reducing agent, taking up oxygen entering the mine after the extinguishing foam subsides, and thereby inhibiting reignition. In the case of a foam concentrate for extinguishing a mine fire, a preferred composition is as follows:

| Ingredient | Weight Percent (%) |
| --- | --- |
| Keratin Protein Hydrolysate | 3.20 |
| $FeSO_4 \cdot 7H_2O$ | 12.00 |
| Dispersant | 4.00 |
| Modified Starch | 5.00 |
| Ammonium hydroxide | 0.60 |
| Biocide | 0.09 |
| Water | 75.11 |

The foam may be generated from the concentrate using the methods described herein. Once generated, the foam is injected into a mine fire site, e.g., by drilling bore holes in the area of a subterranean fire and injecting the foam under pressure, thereby excluding air and extinguishing the fire. Such methods for injection of materials into the area of a mine fire are known and will be readily apparent to those of skill in the art.

EXAMPLE 7

Another exemplary concentrate of the invention is prepared by mixing the following ingredients:

| Ingredient | Weight Percent (%) |
| --- | --- |
| Hydrolyzed Keratin Protein | 3.20 |
| $FeSO_4 \cdot 7H_2O$ | 10.0 |
| Dispersant | 4.0 |
| Modified Starch | 5.00 |
| Ammonium hydroxide | 0.40 |
| Biocide | 0.09 |
| Water | 74.26 |

The concentrate is prepared as described in Example 2. The concentrate is characterized by having a solids content of 15.50%±0.10%; pH, 6.5–7.0 @ room temperature; viscosity, immediately, Brookfield, spindle #4, room temperature, 40000, 22000, 11000, and 6500 cps at 6, 12, 30, 60 rpm, respectively.

The foaming solution is prepared as described in Example 2 above.

EXAMPLE 8

An exemplary dry mixture according to the present invention is prepared by mixing the following ingredients:

| Ingredient | Weight Percent (%) |
|---|---|
| Hydrolyzed Keratin Protein | 21.33 |
| Modified Starch | 50.00 |
| FeSO$_4$ · 7H$_2$O | 28.67 |

This dry mix when diluted at a corresponding D/R=50, i.e., one pound of mix for 49 pounds of water, yields a dilute solution with the following composition:

| | | |
|---|---|---|
| Hydrolyzed Keratin Protein | 4266 | ppm |
| Modified Starch | 10000 | ppm |
| FeSO$_4$ · 7H$_2$O | 5734 | ppm |
| Balance water | 98.00% | |

The foam produced from this diluted composition exhibited a drain time decay rate essentially identical to that of FIG. 4, D/R=4.5.

Numerous modifications and variations of the present invention are included in the above-identified specification and are expected to be obvious to one of skill in the art after having read the foregoing description. Such modifications and alterations to the compositions and processes of the present invention are believed to be encompassed in the scope of the claims appended hereto.

What is claimed is:

1. An aqueous concentrate which upon dilution forms a foam useful as a barrier comprising:

about 2% to about 8%, by weight, hydrolyzed keratin protein;

about 1% to about 7.5%, by weight, hydroxyalkylated starch consisting of at least about 90% amylopectin;

about 1% to about 4%, by weight, ferrous ion;

about 1% to about 10%, by weight, of a dispersant;

a pH modifier, sufficient to adjust the pH to between about 6.5 to about 7; and water.

2. The concentrate according to claim 1, wherein the ferrous ion source is ferrous sulfate.

3. The concentrate according to claim 2, wherein the ferrous sulfate is ferrous sulfate heptahydrate, which is present in an amount of about 5% to about 20%, by weight.

4. The concentrate according to claim 3 comprising about 3.2%, by weight, hydrolyzed keratin protein; about 5%, by weight hydroxyalkylated starch which consists of at least about 99% amylopectin; and about 6%, by weight, ferrous sulfate heptahydrate.

5. The concentrate according to claim 3 comprising about 4.2%, by weight, hydrolyzed keratin protein; about 6.65%, by weight hydroxyalkylated starch which consists of at least about 99% amylopectin; and about 8%, by weight, ferrous sulfate heptahydrate.

6. The concentrate according to claim 1 further comprising a biocide consisting of about 0.1 to about 1%, by weight, of the concentrate.

7. The concentrate according to claim 1, wherein the pH modifier is ammonium hydroxide.

8. The concentrate according to claim 1 further comprising a glycol ether which is present in an amount up to about 2%, by weight.

9. The concentrate according to claim 8 wherein the glycol ether is diethyleneglycol monobutylether.

10. The aqueous concentrate according to claim 1 consisting essentially of 3.2% keratin protein hydrolysate, 12% ferrous sulfate heptahydrate, 4% dispersant, 5% hydroxyalkylated starch, 0.6% ammonium hydroxide, and water, wherein said concentrate is useful for extinguishing mine fires.

11. An aqueous concentrate which upon dilution forms a foam useful as a barrier comprising:

about 2% to about 8%, by weight, hydrolyzed keratin protein;

about 1% to about 7.5%, by weight, hydroxyalkylated starch consisting of at least about 90% amylopectin;

about 1% to about 4%, by weight, ferrous ion;

about 1% to about 10%, by weight, of a dispersant;

a pH modifier, sufficient to adjust the pH to between about 6.5 to about 7;

an odorant; and water.

12. The concentrate according to claim 11, wherein the odorant consists of polymer beads having dispersed thereon cinnamon oil.

13. The concentrate according to claim 11, wherein the odorant is present in an amount up to about 1%, by weight.

14. A dry mixture which upon dilution forms a foam useful as a barrier, said composition comprising, on a dry basis:

about 15% to about 20%, by weight, hydrolyzed keratin protein;

about 25% to about 50%, by weight, hydroxyalkylated starch consisting of at least about 90% amylopectin;

about 6% to about 8%, by weight, ferrous ion; and about 10% to about 15%, by weight, of a dispersant.

15. The mixture according to claim 14 wherein the ferrous ion source is ferrous sulfate.

16. The mixture according to claim 15 wherein the ferrous sulfate is ferrous sulfate heptahydrate which is present in the mixture in an amount between about 30% to about 40%, by weight.

17. The mixture according to claim 16, wherein the ferrous sulfate heptahydrate is about 37%, by weight.

18. The mixture according to claim 14, wherein the hydrolyzed keratin protein is about 19%, by weight.

19. The mixture according to claim 14, wherein the hydroxyalkylated starch consists of at least about 99% amylopectin and is about 30%, by weight.

20. The mixture according to claim 14, wherein the hydroxyalkylated starch is pre-gelatinzed and cold-water soluble.

21. The mixture according to claim 14, wherein the dispersant is about 12%, by weight.

22. The mixture according to claim 21, wherein the dispersant is selected from the group consisting of ammonium lignosulfonate and sodium lignosulfonate.

23. A dry mixture which upon dilution forms a foam useful as a barrier, said composition comprising, on a dry basis:

about 15% to about 20%, by weight, hydrolyzed keratin protein;

about 25% to about 50%, by weight, hydroxyalkylated starch consisting of at least about 90% amylopectin;

about 6% to about 8%, by weight, ferrous ion;

an odorant; and about 10% to about 15%, by weight, of a dispersant.

24. The mixture according to claim 23, wherein odorant consists of polymeric beads having dispersed thereon cinnamon oil.

25. A foamable solution comprising water and about 1 to about 5 weight percent solid actives, wherein said actives comprise:

about 2% to about 8%, by weight, hydrolyzed keratin protein;

about 1% to about 7.5%, by weight, hydroxyalkylated starch consisting of at least about 99% amylopectin;

about 1% to about 4%, by weight, ferrous ion;

about 1% to about 10%, by weight, of a dispersant; and a pH modifier, sufficient to adjust the pH to between about 6.5 to about 7.

26. The foamable solution according to claim 25, wherein the ferrous ion source is ferrous sulfate.

27. The foamable solution according to claim 26 wherein the ferrous sulfate is ferrous sulfate heptahydrate, said solution containing about 5% to about 20%, by weight, ferrous sulfate heptahydrate.

28. The foamable solution according to claim 25 wherein the percent solid actives is about 2 wt %.

29. The foamable solution according to claim 25 wherein the percent solid actives is about 4 wt %.

30. A method of generating a biodegradable foam which comprises the step of:

(a) diluting an aqueous concentrate at a ratio of between 3 to 10 parts by weight water to 1 part by weight concentrate, said concentrate comprising:

about 2% to about 8%, by weight, hydrolyzed keratin protein;

about 1% to about 7.5%, by weight, hydroxyalkylated starch consisting of at least about 90% amylopectin;

about 1% to about 4%, by weight, ferrous ion;

about 1% to about 10%, by weight, of a dispersant; and a pH modifier, sufficient to adjust the pH to between about 6.5 to about 7, and water, thereby obtaining a foamable solution; and (b) agitating the foamable solution of (a) in the presence of air, thereby generating the foam.

31. The method according to claim 30, wherein the aqueous composition is diluted at a ratio of 6.5 parts water to 1 part concentrate.

32. The method according to claim 30, wherein the concentrate comprises about 3.2%, by weight, hydrolyzed keratin protein; about 5%, by weight of the hydroxyalkylated starch which consists of at least about 99% amylopectin, and about 6%, by weight, ferrous sulfate heptahydrate.

33. A foam generated by the method of claim 32.

34. The method according to claim 30, wherein the aqueous composition is diluted at a ratio of 9 parts water to 1 part concentrate.

35. The method according to claim 34, wherein the concentrate comprises about 4.2%, by weight, hydrolyzed keratin protein; about 6.65%, by weight, hydroxyalkylated starch consisting of at least about 99% amylopectin; and about 8%, by weight, ferrous sulfate heptahydrate.

36. A foam generated by the method of claim 35.

37. A method of forming a barrier layer between a substrate and the atmosphere which comprises the steps of:

(a) diluting an aqueous concentrate at a ratio of between 3 to 10 parts by weight water to 1 part by weight concentrate, said concentrate comprising:

about 2% to about 8%, by weight, hydrolyzed keratin protein;

about 1% to about 7.5%, by weight, hydroxyalkylated starch consisting of at least about 90% amylopectin;

about 1% to about 4%, by weight, ferrous ion;

about 1% to about 10%, by weight, of a dispersant; and a pH modified, sufficient to adjust the pH to between about 6.5 to about 7, and water, thereby obtaining a foamable solution;

(b) generating a biodegradable foam from the foamable solution of (a); and (c) applying the foam to a substrate.

38. The method according to claim 37, wherein the aqueous composition is diluted at a ratio of 6.5 parts water to 1 part concentrate.

39. The method according to claim 37, wherein the concentrate comprises about 3.2%, by weight, hydrolyzed keratin protein; about 5%, by weight, hydroxyalkylated starch consisting of at least about 99% amylopectin; and about 6%, by weight, ferrous sulfate heptahydrate.

40. The method according to claim 39, wherein the aqueous composition is diluted at a ratio of 9 parts water to 1 part concentrate.

41. The method according to claim 40, wherein the concentrate comprises about 4.2%, by weight, hydrolyzed keratin protein; about 6.65%, by weight, hydroxyalkylated starch consisting of at least about 99% amylopectin; and about 8%, by weight, ferrous sulfate heptahydrate.

42. A method of extinguishing a mine fire which comprises the steps of:

(a) diluting an aqueous concentrate at a ratio of between 3 to 10 parts by weight water to 1 part by weight concentrate, said concentrate comprising:

about 2% to about 8%, by weight, hydrolyzed keratin protein;

about 1% to about 7.5%, by weight, hydroxyalkylated starch consisting of at least about 90% amylopectin;

about 1% to about 4%, by weight, ferrous ion;

about 1% to about 10%, by weight, of a dispersant;

a pH adjuster, sufficient to adjust the pH to between about 6.5 to about 7, and water, thereby obtaining a foamable solution;

(b) generating a biodegradable foam from the foamable solution of (a); and (c) injecting the foam into a mine at the site of a mine fire, thereby excluding air and extinguishing the fire.

* * * * *